United States Patent [19]

Rootzen et al.

[11] Patent Number: 5,381,195
[45] Date of Patent: Jan. 10, 1995

[54] METHOD AND APPARATUS FOR TESTING A SUBJECT'S PERCEPTION OF VISUAL STIMULI

[76] Inventors: Holger Rootzen, Olshögsvägen 6, S-223 60 Lund, Sweden; Anders Heijl, Danska vägen 62, S-226 39 Lund, Sweden; Jonny Olsson, Fasanvägen 5A, S-227 31 Lund, Sweden

[21] Appl. No.: 35,271

[22] Filed: Mar. 22, 1993

[51] Int. Cl.⁶ .............................................. A61B 3/02
[52] U.S. Cl. ................................... 351/222; 351/237; 351/239; 351/243; 351/246
[58] Field of Search ............... 351/222, 237, 239, 242, 351/243, 246

[56] References Cited

U.S. PATENT DOCUMENTS

| | | | |
|---|---|---|---|
| 3,737,217 | 6/1973 | Haines et al. | 351/237 |
| 3,883,234 | 5/1975 | Lynn et al. | 351/243 |
| 3,905,688 | 9/1975 | Decker et al. | 351/222 |
| 4,255,022 | 3/1981 | Kuether et al. | 351/246 |
| 4,334,738 | 6/1982 | Seckinger | 351/246 |
| 4,429,961 | 2/1984 | Sheingorn | 351/226 |
| 4,697,895 | 10/1987 | Sekiguchi et al. | 351/237 |
| 4,927,259 | 5/1990 | Weber | 351/224 |
| 5,050,983 | 9/1991 | Johnson et al. | 351/226 |
| 5,080,478 | 1/1992 | O'Brien et al. | 351/224 |

FOREIGN PATENT DOCUMENTS

WO92/20282 11/1992 WIPO.

OTHER PUBLICATIONS

Olsson, Jonny et al., "An Image Model For Quantal Response Analysis in Perimetry", Center for Stochastic Processes, University of North Carolina, Technical Report No. 355, pp. 1–26, Nov. 1991.

Jonny Olsson, "Statistics in Perimetry", Department of Mathematical Statistics, Lund University, 1991, pp. 1–39 and Appendices H–K.

Primary Examiner—Richard A. Bertsch
Assistant Examiner—Howard R. Richman
Attorney, Agent, or Firm—Burns, Doane, Swecker & Mathis

[57] ABSTRACT

In a method of testing a subject's perception of successively presented visual stimuli, a predetermined preliminary response time window is used at the beginning of the test to preliminarily classify the visual stimuli as "seen" or "not seen" depending on whether or not a response is received from the subject within the preliminary response time window. To permit reclassification of the visual stimuli at a later stage, the time of reception of every response, whether outside or within the preliminary response time windows, is stored. When an appropriate number of stimuli have been presented, a subject-adapted response time window is determined on the basis of the stored times of reception of the responses. This subject-adapted response time window is used for reclassifying the preliminarily classified stimuli. Moreover, the frequency of false positive responses can be determined on the basis of the number of responses received outside the preliminary response time window and/or the subject-adapted response time window. An apparatus for carrying out the testing includes a control unit operating according to the method.

22 Claims, 4 Drawing Sheets

METHOD AND APPARATUS FOR TESTING A SUBJECT'S PERCEPTION OF VISUAL STIMULI

FIELD OF THE INVENTION

The present invention relates to visual testing, and in particular to an improved method and apparatus for assessing a subject's responses to visual stimuli.

BACKGROUND OF THE INVENTION

Perimetry is a very important and common test in clinical eye care, second only to the simple determination of visual acuity. It is used for examining the range and the sensitivity of a subject's visual field, e.g. in connection with diagnosis and treatment of glaucoma, for testing for neurological diseases, in mass screening etc.

In static threshold perimetry, the limit or threshold of a subject's light perception at a number of discrete locations in the visual field is determined. The test is conducted by means of a computerized perimeter, typically in the following way: the patient is seated in front of a perimeter and asked to look steadily at a centrally placed fixation target, e.g. on a screen or in a hemispheric bowl. Visual stimuli are presented successively with different intensities and at different locations. The patient is asked to press a response button every mime he perceives a stimulus, whether close to or distant from the fixation target, whether faint or strong.

There are different methods for presenting stimuli to the patient in order to establish his threshold for perception of light. One common method consists in showing a stimulus having an intensity close to the expected threshold value at the test location concerned. If the patient does not respond to the stimulus, the intensity of the subsequently presented stimuli is thereafter increased stepwise until a response is received from the patient, i.e. until a stimulus is seen. The first intensity level at which a response is received can be defined as the threshold of the test location concerned. The precision of the test can be increased by reversing the test process when the first response is received, and by continuing it in smaller steps until the first unseen stimulus is encountered. The threshold can then be defined as the average intensity level of the last seen stimulus and the first unseen stimulus. If, on the other hand, the patient responds to the first stimulus, the intensity is gradually decreased until no response is received, whereupon the test procedure is reversed. In this context, it should be pointed out that the test locations are usually tested in random order, a stimulus at a first test location being followed by a stimulus at another test location etc., and the next stimulus for the first test location being not presented until after several subsequent stimulus presentations.

When the threshold values for all the test locations in the visual field have been determined, they are often compared with normal, previously determined threshold values for patients of the same age to establish whether there are any deviations from normal, or with previous values for the same eye of the patient to establish whether a disease under observation has progressed or receded.

One problem inherent in static threshold perimetry is that it is time-consuming. As described above, several stimuli of different intensity are presented at each test location on the screen. Since usually 50-100 test locations are examined, one test consists of several hundred stimulus presentations. Typically, the time required for a complete static threshold perimetry test is about 10-20 minutes per eye. The test is very tiring, which may affect the test accuracy.

Furthermore, even though the test procedure is computerized, an operator must usually be present during the test to ensure that the patient maintains fixation, to encourage him and to answer any questions he may have.

Another problem of static threshold perimetry is the assessment of the responses from the patients. After each presentation of a stimulus, the perimeter waits for a response during at most a predetermined time period. If no response is received during the predetermined time period, the stimulus has usually not been seen, and if a response is received, the stimulus has usually been seen. However, it is well-known that patients sometimes press the button without having seen any stimulus at all, and they sometimes fail to press it despite having seen the stimulus. These kinds of responses are called false positive responses and false negative responses, respectively. It goes without saying that it is important to minimize the number of false positive responses and false negative responses to keep the measurement error level as low as possible. The frequency of false positive responses is examined by false positive catch trails. The perimeter acts as when displaying a stimulus without showing one and registers whether the patient responds or not. The frequency of false negative responses is examined by false negative catch trials. A strong, supraliminal stimulus is presented at a location where the threshold has already been measured and the perimeter registers whether the patient responds or not. Usually 20-30 catch trials are presented during a test.

Many suggestions have been made for shortening the total time required for performing static threshold perimetry. Most of them have aimed at reducing the number of presentations of stimuli. One example is given in Heijl A, Krakau CET: An automatic perimeter for glaucoma visual field screening and control; Albrecht v. Graefes Arch. Clin Exp. Ophthalmol 197:13-22, 1975. Another example is given in U.S. Pat. No. 4,334,738 describing a method for better selecting the intensity level for the first stimulus presented at each test location, whereby the number of presentations of stimuli required for arriving at a threshold value, can be reduced. A further example is disclosed in U.S. Pat. No. 4,927,259 where the intensity is varied by logarithmic steps between stimuli for one test location.

Fewer suggestions aim at shortening the time between the presentation of stimuli. Most of the testing time is in fact used for awaiting a response from the patient. Traditionally, a fixed maximum waiting time between stimuli is set before the commencement of the test, and is thereafter used throughout the test. If the patient does not respond to a stimulus, the perimeter must wait all the fixed maximum waiting time before the next stimulus is presented. If, on the other hand, the patient responds, a new stimulus can be presented a certain time after the response has been received. In general, it is not possible to shorten the fixed maximum waiting time between successively presented stimuli, for this would involve the risk of missing responses from slow patients, which would decrease the reliability of the test.

DE 31 35 384 discloses the use of a variable waiting time consisting of the patient's mean reaction time plus a statistically varying time addition. By this variable waiting time, it is taken into account that the patient's reaction time at the beginning of the test is shortened owing to test learning, and is prolonged at the end of the test owing to test tiredness. Also EP 0 163 674 describes the use of a variable waiting time based on the patient's mean reaction time. Here, the test is interrupted if the patient's reaction time increases too much, for, if so, the patient is considered to be tired and the test result to be unreliable.

SUMMARY OF THE INVENTION

One object of the present invention is to provide an improved method and apparatus for assessing the responses from patients to visual stimuli.

Another object of the invention is to provide a method and an apparatus which permit shortening the time for testing a subject's perception of light without any rise of the measurement error.

A further object is to provide a method and an apparatus which permit reducing the number of false positive catch trials.

These objects are achieved by a method according to the appended method claims.

Thus, according to one aspect of the method, an individual or subject-adapted response time window is determined for each patient based on the recorded times of reception of the patient's responses to visual stimuli, and the subject-adapted response time window is used for classifying previously presented visual stimuli. However, in some kinds of tests the visual stimuli must be classified as they are presented because the classification is decisive of the strength of subsequently presented stimuli.

But, before commencing a test, there are no response times on which to base the determination of an individual response time window. According to a further aspect of the method, a predetermined preliminary response time window, preferably computed from known parameters for a population to which the patient belongs, is used at the beginning of the test to preliminarily classify the visual stimuli as "seen" or as "not seen". Thus, contrary to prior-art methods, the visual stimuli are not finally classified when received. To permit reclassification of the visual stimuli at a later stage, the time of reception of every response, whether outside or within the preliminary response time windows, is stored in a memory. When an appropriate number of visual stimuli have been presented, which may be during the test or after the presentation of visual stimuli has been terminated, a subject-adapted response time window is determined based on the stored times of reception of the responses. This subject-adapted response time window is applied to the stored response times for reclassifying some or all of the preliminarily classified visual stimuli according to the subject-adapted response window.

Preferably, subject-adapted response time windows are computed several times during a test to take account of the responses received at a later stage of the test. However, it is not necessary to reclassify the previously presented stimuli every time a subject-adapted response time window is computed. During the test, it may suffice to use the subject-adapted response time windows for preliminarily classifying subsequently presented visual stimuli. However, after the presentation of visual stimuli has been terminated all presented visual stimuli are preferably finally classified by means of a final subject-adapted response time window.

According to a further aspect of the method, the subject-adapted response time window is used for classifying at least one visual stimulus presented subsequent to the determining of the subject-adapted response time window, and the frequency of false positive responses is determined on the basis of the number of responses received outside the preliminary response time window and the subject-adapted response time window.

The method according to the present invention is less time-consuming than prior-art methods. Since the response time windows are individual, shorter intervals between successive visual stimuli can be employed, which is time-saving in those cases where the patient does not respond to a stimulus. Small or no safety margins at all need be added for slow patients. Moreover, false positive catch trials are no longer required since the frequency of false positive responses may be determined from the number of responses received in the time period between the different response time windows. By means of the present invention, the total time required for performing a static threshold perimetry test may be decreased by 15–30% as compared with clinically employed methods.

Furthermore, owing to the subject-adapted response time windows, the classification of the visual stimuli is more reliable and the number of false positive and/or false negative responses is reduced, which in turn increases the accuracy of the determination of the threshold values.

The above-mentioned objects are also achieved by an apparatus according to the appended apparatus claim.

The present invention is applicable to different types of visual tests, e.g. in perimetry, both in screening where only one or a few stimuli are presented for each test location, and in static or dynamic threshold perimetry.

The present invention may confer the same advantages also in other visual tests where the patient is instructed to respond when perceiving a stimulus, and not to respond when not perceiving a stimulus. Examples of such tests are computerized, central or peripheral visual acuity testing, or determination of contrast sensitivity. In these kinds of tests, all stimuli may be presented in one location only, but the stimuli may have different appearances and each threshold value may be related to stimuli of a specific appearance.

In screening tests, all presented stimuli may be of the same strength, but in threshold tests, visual stimuli of different strengths are presented to check or determine the threshold values of the subject under test. The strength of the stimuli is often the intensity of the stimuli, but may as well be the color, the size, the color saturation, the spatial frequency, the flicker frequency or any other parameter thereof which can be varied.

The above-mentioned and other objects and features of the present invention will become more apparent from a consideration of the following detailed description in conjunction with the accompanying drawings.

DESCRIPTION OF THE PREFERRED EMBODIMENT

Figure 1:
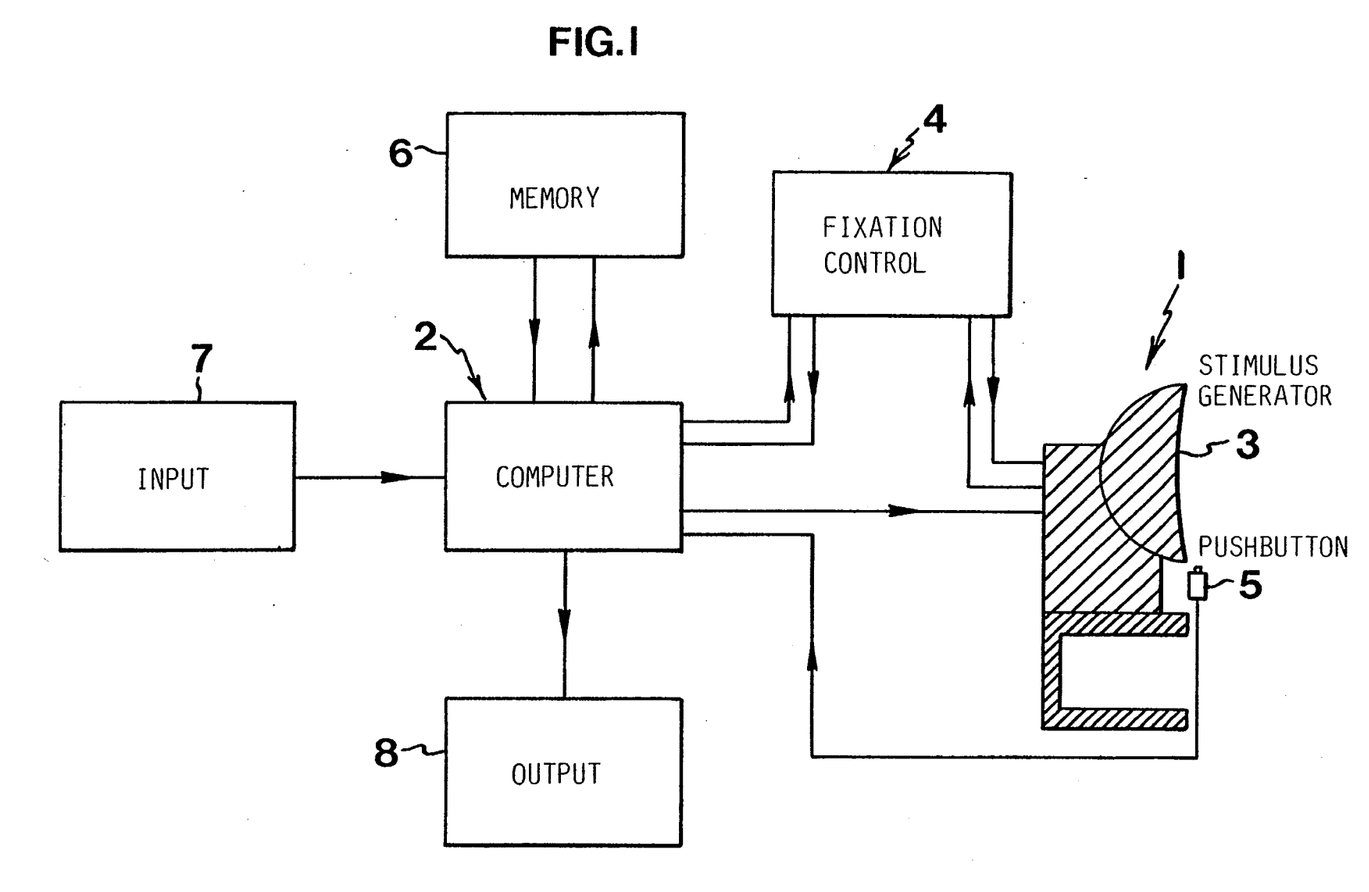
FIG. 1 schematically shows a computerized perimeter.

FIG. 1 shows schematically, partly in the form of a block diagram, the design of a computerized perimeter, by means of which the method of the invention can be carried out. The perimeter consists essentially of a stimulus generator 1 and a computer 2 for controlling the generator and for assessing the responses to presented stimuli that are received from the patient.

The stimulus generator 1 has a hemispherical screen 3, in front of which the patient is seated. The screen is provided with a fixation target, for example in the form of a light-emitting diode which is shining continuously and at which the patient is asked to look throughout the test. The stimulus generator 1 serves to provide well-defined visual stimuli at selected locations on the screen, which should be evenly illuminated. These stimuli can be generated by means of a projection system or by means of fixed light sources (light-emitting diodes or optical fibers) or any other suitable means.

Advantageously, the perimeter also has means 4 for monitoring the patient's fixation of the fixation target, such that stimuli that are presented when the patient is blinking or does not maintain fixation can be sorted out or repeated. The fixation monitoring function may be implemented electronically or with the aid of a TV-camera. Other types of fixation monitoring are of course also possible.

The perimeter further comprises a press button 5, by means of which the patient should give a response each time he sees a visual stimulus on the screen. Responses may also be obtained by measuring pupillary responses or visually evoked potentials or by any other suitable means. The press button 5 is connected to the computer 2 which assesses every response from the patient and, on the basis thereof, determines the location and the intensity of the next visual stimulus in compliance with a control program stored in the computer. The computer has a memory 6, in which for example the responses to the stimuli are stored. The computer is also provided with an input unit 7, by means of which an operator can supply information to the perimeter, and an output unit 8, by means of which the results of the visual field tests are presented. The input unit 7 may, for example, consist of a keyboard and the output unit 8 of a printer or a display device.

The physical design of the perimeter described above does not differ from that of prior-art perimeters. As will be explained hereinafter, the perimeter of the invention is however operated in a completely new manner, allowing shorter overall testing times with the aid of a new control program in the computer.

Figure 2:
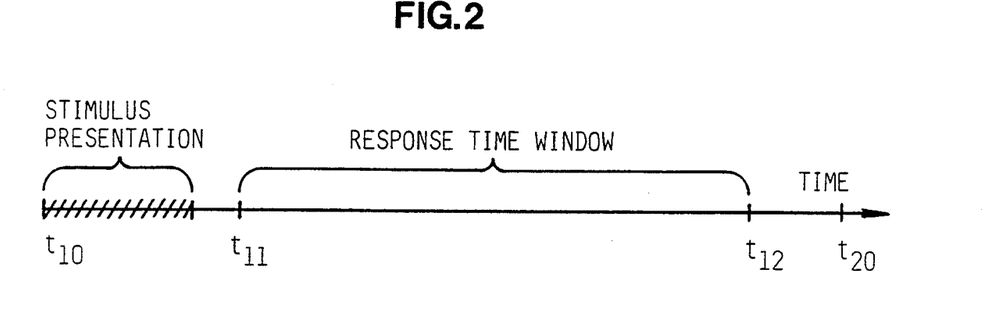
FIG. 2 is a time axis on which a visual stimulus and a pertaining response time window are shown.

FIG. 2 schematically shows the progress of a part of a visual field test according to the invention. At time t10, a visual stimulus is presented. Its duration is normally 200 ms, as shown by oblique lines. At time t11, a response time window starts. It lasts to time t12. The presentation of the next stimulus is started either shortly after a response has been received or shortly after the end of the response time window, at time t20. It should here be pointed out that the response time windows can start during the very presentation of the stimulus.

During the test, a response given in the response time window, i.e. between t11 and t12, results in that the presented stimulus is preliminarily recorded as "seen". A response received between t10 and t11, or between t12 and t20, is preliminarily considered as a false positive response. If no response is received in the response time window, the visual stimulus is recorded as "not seen".

According to the present invention, the length of the response time window is adapted to the test subject. This is done by determining one or more subject-adapted response time windows during and/or after the test on the basis of response times of stimuli previously presented during the test.

The subject-adapted response time windows may be used for preliminarily classifying subsequently presented stimuli and/or be applied to the recorded response times for classifying anew previously presented stimuli. It may then occur that stimuli previously classified as "seen" prove to be false positive responses, or vice versa. Such a reclassification may affect the continued testing of the patient.

Figure 3A:
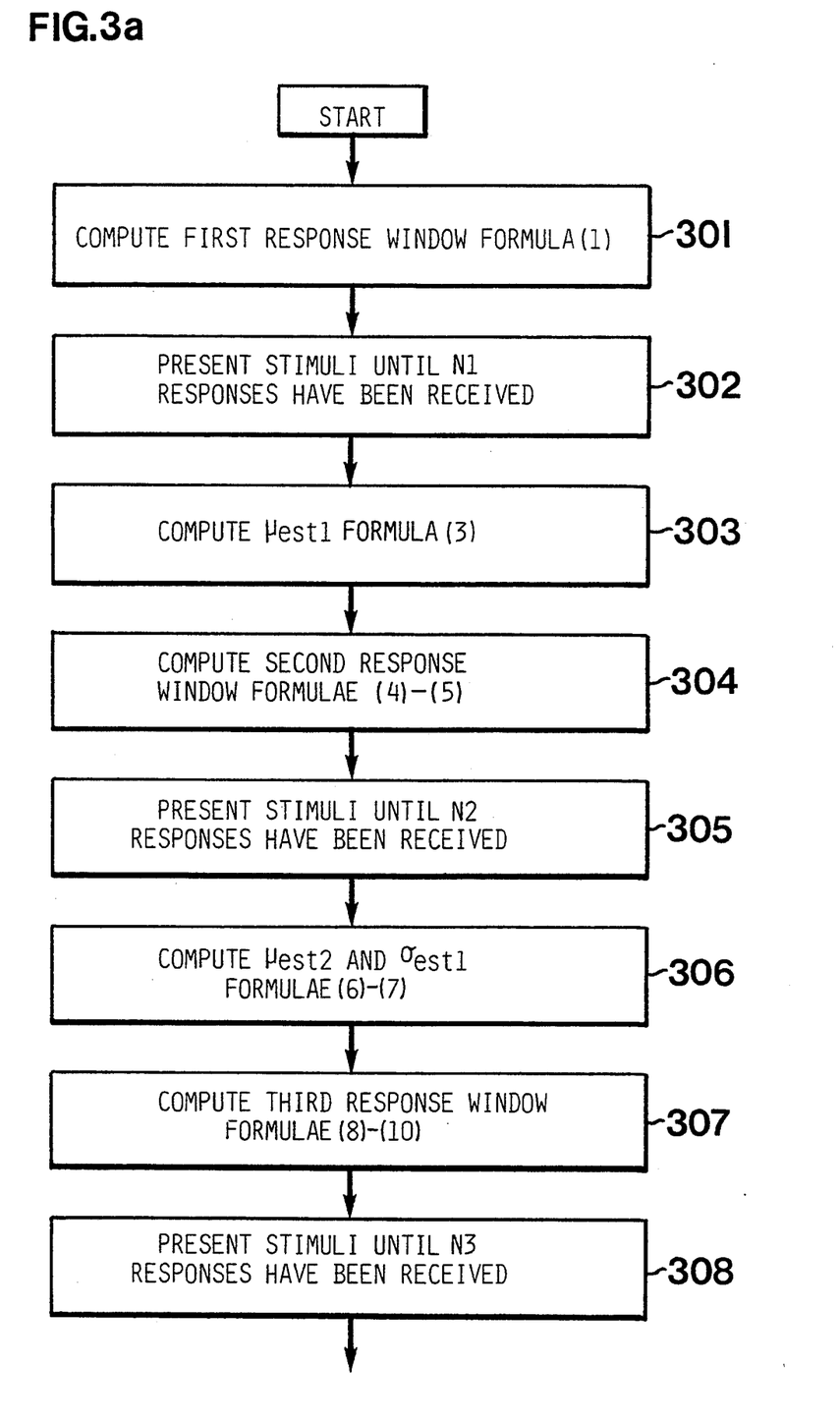
FIG. 3A and B shows a flow diagram of a method for performing visual field testing according to the present invention.
Figure 3B:
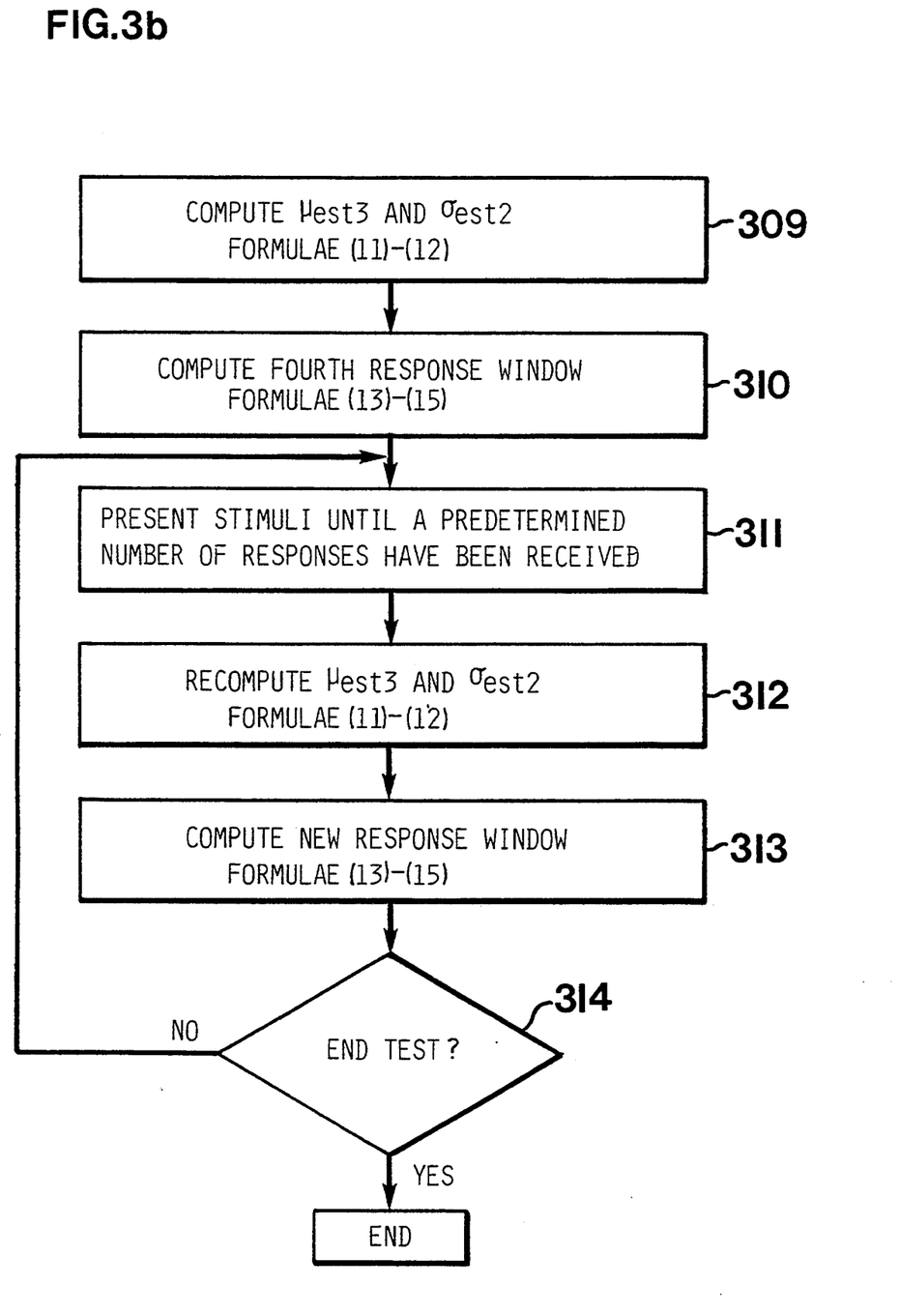

FIG. 3 shows a flow diagram of the method according to the invention. The visual field test starts in box 301 by calculating a first preliminary response time window. If the patient has previously been examined, there may already be information available on previously employed response time windows that can be used again. If, however, the patient is examined for the first time, there are no data available before the test on which to base a subject-adapted response time window. Therefore, to calculate a first preliminary response time window, use is made of known parameters for a population to which the patient belongs. The parameters used are the mean value $\mu_{pop}$ for the log-normal distribution of the response times exceeding 250 ms for the population to which the patient belongs, the standard deviation $\sigma_{pop}$ for said log-normal distribution, the variance $V(\mu_{pop})$ of the above-mentioned mean value, and the variance $V(\sigma_{pop})$ of the above-mentioned standard deviation. In this context, it should be pointed out that if one only uses response times above 250 ms and makes a logarithm thereof, a normal distribution is obtained.

On the basis of the above parameters, the maximum time limit $RT_{max}$, i.e. the end of the response time window is calculated according to the following formula (1):

$$\ln(RT_{max}(x) - 250) = \mu_{pop} + \beta x + \lambda_1 \sigma_{pop} + \lambda_2 \sqrt{V(\mu_{pop}) + x^2 V(\beta) + \lambda_1^2 V(\sigma_{pop})},$$

wherein $\beta$ is a regression coefficient which reflects the dependence of the response times on the stimulus intensity and which can be calculated by linear regression, $V(\beta)$ is the variance of the regression coefficient $\beta$ in the population, $\lambda_1$ and $\lambda_2$ are empirically determined constants, typically having a value close to 2, and x is the difference between the stimulus intensity in an examined point in the visual field and the normal threshold value for this point. Possibly, a constant value may be added to the maximum time limit $RT_{max}$ to take account of the fact that the determination of the maximum time limit is based on already received responses, but the response time window determined from the maximum time limit is used for subsequent responses.

The maximum time limit $RT_{max}$ for this first preliminary response time window is thus allowed to vary by x, i.e. by the stimulus intensity. The reason for this is that it has been found in tests that the response time decreases with increasing stimulus intensity.

The minimum time limit $RT_{min}$, i.e. the beginning of the response time window, can be calculated according to the following formula (2):

$$\ln(RT_{min}(x) - 250) = \mu_{pop} + \beta x + \lambda_1 \sigma_{pop} + \lambda_2 \sqrt{V(\mu_{pop}) + x^2 V(\beta) + \lambda_1^2 V(\sigma_{pop})},$$

In a preferred embodiment of the invention, the minimum time limit $RT_{min}$ is however set at a constant value, e.g. 180 ms, since it varies but to a very small extent.

As appears from the above, the first preliminary response time window does thus not have a constant length, the length being actually determined by a constant value plus a factor depending on the intensity of each stimulus. For greater clarity, all response time windows based on the first preliminary response time window, whose length differs only by an intensity-depending factor, are however referred to as the first preliminary response time window.

When this first preliminary response time window has been calculated, a plurality of stimuli are successively presented in accordance with box 302, and the times are recorded for any responses received to these stimuli. The stimuli are preliminarily classified as follows: if no response is received in the response time window for a stimulus, this stimulus is preliminarily classified as "not seen". If a response is received in the response time window, the stimulus is classified as "seen". Responses received outside the response time window do not affect the preliminary classification of the stimuli, but the times of the reception of all responses are recorded in the same way as for responses received in the response time windows.

After a predetermined number, e.g. N1=10, of responses to the visual stimuli have been received, a first estimation is made according to box 303 of the mean value $\mu_{est1}$ of lognormal distribution of the patient's response times. The mean value $\mu_{est1}$ is calculated according to the following formula (3):

$$\mu_{est1} = \frac{1}{N1} \sum_{i=1}^{N1} (\ln(r_i - 250) - \beta(x_i - \bar{x}_{est1})),$$

wherein $r_i$ is the i:th response time, $x_i = d_i - n_i$ is the stimulus intensity for the i:th response minus the normal threshold value for the point in which the stimulus corresponding to the i:th response is presented and $\bar{x}_{est1}$ is equal to the mean value of $x_i$, where $i = 1, 2, \ldots, N1$.

On the basis of this estimated mean value $\mu_{est1}$, a second preliminary response time window is thereafter calculated according to box 304, this response time window being thus partly adapted to the patient being tested. The maximum time limit $RT_{max}$ for the second preliminary response time window is calculated according to the following formula (4):

$$\ln(RT_{max}(x) - 250) = \mu_{est1} + \beta(x - \bar{x}_{est1}) + \lambda_1 \sigma_{pop} + \lambda_2 \sqrt{V(\mu_{est1}) + (x - \bar{x}_{est1})^2 V(\beta) + \lambda_1^2 V(\sigma_{pop})}$$

wherein the variance $V(\mu_{est1})$ is calculated according to the following formula (5):

$$V(\mu_{est1}) = \sigma_{pop}^2/(N1)$$

In the same way as for the first preliminary response time window, the maximum time limit $RT_{max}$ for the response time window is calculated, while the minimum time limit $RT_{min}$ is set at a constant value. It is however possible to calculate the minimum time limit $RT_{min}$, if so desired, in a similar manner as for the first preliminary response time window. The length of the second preliminary response time window is determined in the same way as the first by a constant value plus a factor depending on the stimulus intensity. All the response time windows based on formula (4) are however referred to as the second preliminary response time window.

Then, an additional plurality of stimuli are presented according to box 305, the response times are recorded for any responses given to these stimuli, and the stimuli are preliminarily classified by means of the second preliminary response time window.

When a predetermined number, e.g. N2=15, of additional responses to the stimuli have been received, a new estimated mean value $\mu_{est2}$ as well as an estimated standard deviation $\sigma_{est1}$ can be calculated for the patient (box 306) according to the following formulae (6)-(7):

$$\mu_{est2} = \frac{1}{N1 + N2} \sum_{i=1}^{N1+N2} (\ln(r_i - 250) - \beta(x_i - \bar{x}_{est2})),$$

$$\sigma_{est1}^2 = \max\left( 0.2^2, \min\left( 0.6^2, \frac{\sum_{i=1}^{N1+N2} ((\ln(r_i - 250) - \beta(x_i - \bar{x}_{est2})) - \mu_{est2})^2}{N1 + N2 - 1} \right) \right)$$

wherein $\bar{x}_{est2}$ is equal to the mean value of $x_i$, where $i=1, 2, \ldots N1+N2$.

These new patient parameters $\mu_{est2}$ and $\sigma_{est1}$ are used for calculating a third preliminary response time window in accordance with box 307. For calculating the maximum time limit $RT_{max}$ for the third preliminary response time window, the following formulae (8)-(10) are used:

$$\ln(RT_{max}(x) - 250) = \mu_{est2} + \beta(x - \bar{x}_{est2}) + \lambda_1 \sigma_{est1} + \lambda_2 \sqrt{V(\mu_{est2}) + (x - \bar{x}_{est2})^2 V(\beta) + \lambda_1^2 V(\sigma_{est1})}$$

$$V(\mu_{est2}) = \sigma_{est1}^2/(N1 + N2)$$

$$V(\sigma_{est1}) = \sigma_{est1}^2/(2(N1 + N2 - 1))$$

What has been stated above in respect of the maximum time limit and the minimum time limit and the dependence of the length of the response time window on the stimulus intensity also applies to the third preliminary response time window.

The third preliminary response time window is used in accordance with box 308 for the following stimuli. As previously done, the stimuli are presented, the response times are recorded for any responses received to the stimuli, and the presented stimuli are preliminarily classified by means of the third response time window.

In accordance with box 309, new more reliable patient-adapted parameters are calculated after a predetermined number, e.g. N3=10, of additional responses have been received, in the form of a mean value $\mu_{est3}$ and a standard deviation $\sigma_{est2}$. The following formulae (11) and (12) are used:

$$\mu_{est3} = \text{median}_{i=1,\ldots,N1+N2+N3}(\ln(r_i - 250) - \beta(x_i - x_{est3}))$$

$$\sigma_{est2} = \max(0.2, \min(0.6, (\text{median}_{i=1,\ldots,N1+N2+N3}|(\ln(r_i - 250) - \beta(x_i - x_{est3})) - \mu_{est3}|/0.6745))$$

wherein $\bar{x}_{est3}$ is equal to the mean value of $x_i$, where $i=1, 2, \ldots, N1+N2+N3$.

According to these formulae, responses received close to the beginning or the end of the response time window affect the patient parameters less than responses received in the middle of the response time window. In this way, a false positive response close to the limits of the response time window does not offset the mean value to any significant extent.

The thus calculated patient parameters $\mu_{est3}$ and $\sigma_{est2}$ are used for computing a maximum time limit $RT_{max}$ for a fourth preliminary response time window (box 310) according to the following formulae (13)–(15):

$$\ln(RT_{max}(x) - 250) = \mu_{est3} + \beta(x - x_{est3}) + \lambda_1 \sigma_{est2} + \lambda_2 \sqrt{V(\mu_{est3}) + (x - x_{est3})^2 V(\beta) + \lambda_1^2 V(\sigma_{est2})}$$

$$V(\mu_{est3}) = (\sigma^2_{est2}/(N1 + N2 + N3))/0.637$$

$$V(\sigma_{est2}) = \sigma^2_{est2}/(2(N1 + N2 + N3 - 1)))/0.368$$

The fourth preliminary response time window is used in accordance with box 311 for the following stimuli. When e.g. 40 additional responses have been received, the patient parameters $\mu_{est3}$ and $\sigma_{est2}$ are recalculated according to formulae (11) and (12) (box 312) with N3=10+40=50, and a new preliminary response time window is calculated according to formulae (13)–(15) (box 313) also with N3=50. The new preliminary response time window is used for the following stimuli until 75 additional responses have been received. The test thereafter proceeds in the same way with a recalculation of patient parameters $\mu_{est3}$ and $\sigma_{est2}$ and new preliminary response time windows every 75 responses until the test is completed (box 334). It should be pointed out that the recalculation of $\mu_{est3}$ and $\sigma_{est2}$ and the new preliminary response time windows is based only on the 75 latest received responses thus N1+N2+N3=75 and not on fact that the patient parameters $\mu$ and $\Sigma$ may change during the test due to test learning and/or test fatigue.

After the test proper has been completed, a final classification is made of all the stimuli presented. The final classification is made in accordance with the flow diagram in FIG. 4. First, all the responses received are divided into groups, each including 50 responses (box 401). Then, calculation (box 402) is made of the mean value $\mu_{est3}$ and the standard deviation $\sigma_{est2}$ for the lognormal distribution of the response times in each group according to formulae (11) and (12) with appropriate index i values (N1+N2+N3=50). Furthermore, the variance $V(\mu_{est3})$ of the mean value $\mu_{est3}$ of each group and the variance $V(\sigma_{est2})$ of the standard deviation $\sigma_{est2}$ of each group are calculated according to formulae (14) and (15) with N1+N2+N3=50. In the next step (box 403), an individual mean value $\mu_{est3}(r_i)$, is established, wherein i=1, 2, ..., the number of responses received, for each response received by interpolation of the sequence of the mean value for the groups, the mean value being assigned to the response in the middle of each group. In the following step (box 404) is established, for each response received, an individual average intensity difference value $\bar{x}_{est3}(r_i)$, where i=1, 2, ..., the number of responses received. On the basis of the calculated individual mean values $\bar{x}_{est3}(r_i)$ and the individual average intensity difference values $\bar{x}_{est3}(r_i)$, is thereafter calculated (box 405) a final response time window for each presented stimulus according to formula (13), the standard deviation $\sigma_{est2}$ being set at the mean value of the standard deviations for the groups, the variance $V(\sigma_{est2})$ being set at the mean value of the variances $V(\sigma_{est2})$ for the groups divided by the number of groups, the variance $V(\mu_{est3})$ being set at the mean value of the variances $V(\mu_{est3})$ for the groups, and the variance $V(\beta)$ being set at the same constant as in formula (1).

Figure 4:
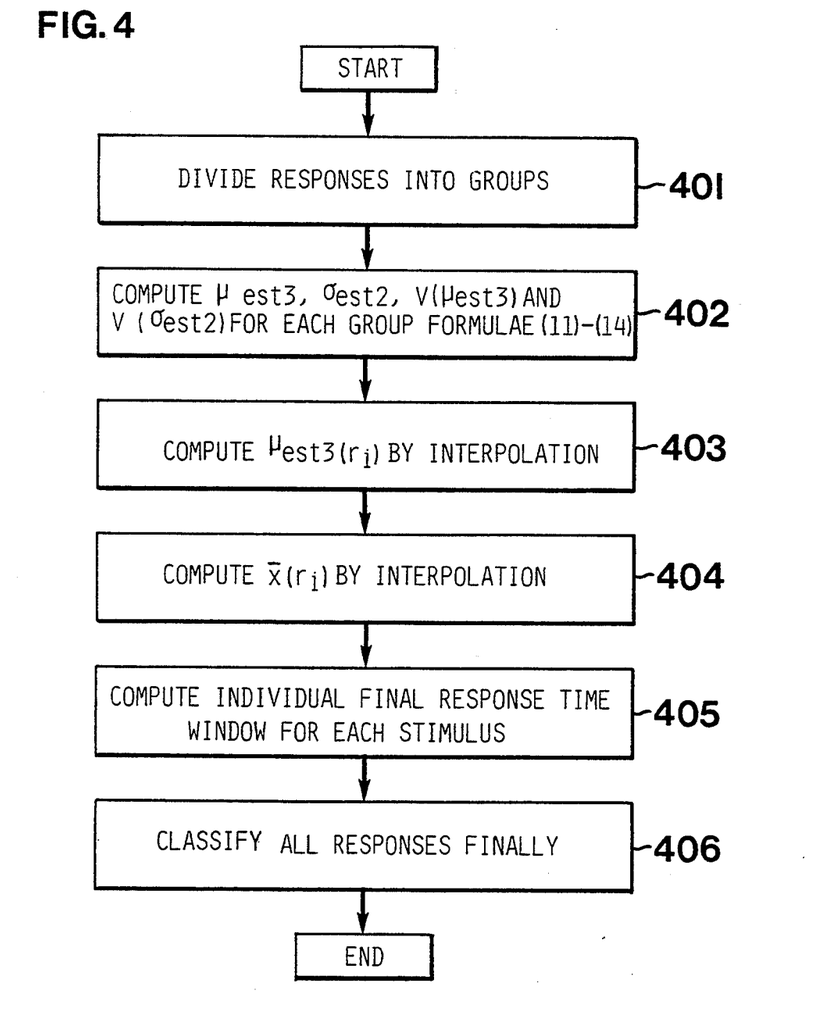
FIG. 4 is a flow diagram showing how a final reclassification of visual stimuli is performed according to the method of the present invention.

When the individual response time windows have been set, it is suitably checked that each individual window is not longer than the time period between the stimulus for the classification of which it is to be used, and the following stimulus. If the response time window exceeds this time period by more than the reaction time of the patient, it may in fact be difficult to determine to which stimulus a response pertains. If many individual response time windows are too long, the stimulus presentation is likely to have taken place too quickly and should perhaps be repeated.

On the basis of the individual response time windows, the stimuli are then finally classified (box 406). It may then occur that a stimulus which during the progress of the test was classified as "seen" due to 406). It may then occur that a stimulus which during the progress of the test was classified as "seen" due to the fact that the response was received within the response time window then applied, is reclassified as "not seen" because the response was received outside the final response time window and the response therefore is finally classified as a false positive response, and vice versa.

After the final classification, test locations with uncertain responses may be fetested or cancelled from the test result. Moreover, the frequency of false positive responses can be calculated on the basis of the number of responses received outside the time response windows and the total time not made up by response time windows.

Thereafter, the threshold values of all test locations are finally determined by some appropriate method based on the finally classified stimuli.

The result of the test is usually presented on one or more maps. On one map, the threshold values may be numerically presented at the respective test locations. On another map, the threshold values may be presented by gray-scale representation. On a further map, the deviation of each threshold value from the normal expected value at its test location may be numerically presented. On still another map, the significances of physician to diagnose glaucoma and other eye diseases and to decide on the treatment thereof.

The result of other visual tests may be presented in a similar way.

The computerized perimeter shown in FIG. 1 preferably has a control program for controlling the perimeter for operation according to the method described above. Such a control program can be achieved by those skilled in the art on the basis of the embodiment described above and, therefore, will not be discussed in more detail here.

Many modifications to the preferred embodiment are possible. Stimuli may be presented on a spherical or flat surface, or even as an image in space.

Stimuli may be simple and well-defined white circular stimuli against an even, white background, which is typical in today's clinical perimetry. Stimuli may, however, also be of almost any other character, e.g. colored, composed of high- or low-contrast gratings or moving bars of light, consisting of multiple components or even complex images.

Further, in the preferred embodiment, the determination of the subject-adapted response time window is based on the mean value and the standard deviation of a log-normal distribution of the response times. However, the response times may be assumed to be distributed according to another distribution of nonnegative random variables, e.g. a log-logistic distribution, a Weibull distribution, a γ-distribution, an F-distribution etc.

Moreover, it is not necessary to reclassify or finally classify all previously presented stimuli. It may suffice to reclassify only those stimuli which were presented in the beginning of the test.

Evidently the number of responses received between the computations of the different response time windows may differ from the numbers disclosed in the preferred embodiment. For example the response time window may be recomputed for every visual stimulus presented.

What we claim and desire to secure by Letters Patent is:

1. A method of testing a subject's response to visual stimuli, comprising the steps of:
   successively presenting a plurality of visual stimuli to the subject;
   detecting whether the subject responds to each stimulus and, for each stimulus to which a response is detected, recording the time of the subject's response;
   determining a subject-adapted response time window based upon recorded times; and
   classifying at least some of the presented stimuli as "seen" or "not seen" in dependence upon whether a response to the stimulus was detected within the subject-adapted response time window following the presentation of the stimulus.

2. A method of testing a subject's perception of successively presented visual stimuli, comprising the steps of:
   determining a preliminary response time window,
   presenting at least one visual stimulus to the subject, and for said at least one visual stimulus:
   waiting for a response during at most a predetermined time period,
   recording the time of reception of any response received from the subject within said predetermined time period,
   preliminarily classifying said at least one visual stimulus as "seen" if a response is received within said preliminary response time window and otherwise as "not seen",
   determining a subject-adapted response time window based on recorded times of reception of previously received responses,
   classifying anew said at least one preliminarily classified visual stimulus by applying the subject-adapted response time window, said at least one preliminarily classified visual stimulus being classified as "seen" if the associated response was received within said subject-adapted response time window, and otherwise as "not seen".

3. A method according to claim 2, wherein said step of presenting at least one visual stimulus to the subject comprises the step of modifying for each presented visual stimulus the response time window by a factor, the value of which depends on the strength of said each presented visual stimulus.

4. A method according to claim 2, wherein said step of classifying anew said at least one preliminarily classified visual stimulus comprises the step of modifying the subject-adapted response time window for said response by a factor, the value of which depends on the intensity of said at least one preliminarily classified visual stimulus.

5. A method according to claim 2, wherein said step of determining a subject-adapted response time window further comprises the steps of:
   assuming that said recorded times of reception are distributed according to a distribution of non-negative random variables,
   computing the mean value and the standard deviation of said distribution of non-negative random variables,
   basing said determining of a subject-adapted response time window on said mean value and said standard deviation.

6. A method according to claim 2, wherein said step of determining of a subject-adapted response time window further comprises the steps of:
   assuming that said recorded times of reception, after subtraction of a constant, are distributed according to a log-normal distribution,
   computing the mean value and the standard deviation of said log-normal distribution, and
   determining said subject-adapted response time window based on said mean value and said standard deviation of said log-normal distribution.

7. A method according to claim 2, wherein said step of determining of a subject-adapted response time window further comprises the steps of:
   transforming said recorded times of reception to a log-normal distribution by subtracting a constant from and taking the logarithm of each said recorded times of reception,
   computing the mean value and the standard deviation of said log-normal distribution, and
   determining the end limit of said subject-adapted response time window based on the exponential of said mean value and on at least one said standard deviation and on a safety factor, the value of which depends on the intensity of said at least one preliminarily classified stimulus.

8. A method according to claim 2, further comprising the step of using said subject-adapted response time window for preliminarily classifying at least one visual stimulus presented subsequent to said determining of said subject-adapted response time window.

9. A method according to claim 2, wherein said step of determining of a subject-adapted response time window is repeated several times during the testing of a subject.

10. A method according to claim 2, wherein said steps of determining a subject-adapted response time window and of classifying anew said at least one preliminarily classified visual stimulus are carried out after the presentation of visual stimuli has been terminated.

11. A method according to claim 10, wherein the frequency of false positive responses is determined on the basis of the number of responses received outside said subject-adapted response time window.

12. A method of testing a subject's perception of successively presented visual stimuli, each stimulus having a selected strength, comprising the steps of:
   determining a preliminary response time window,
   presenting a plurality of visual stimuli to the subject, and for a presented visual stimulus:
   modifying the preliminary response time window by a factor, the value of which depends on the strength of said each presented visual stimulus,
   waiting for a response during at most a predetermined time period,
   recording the time of reception of any response received from the subject within said predetermined time period,
   preliminarily classifying said presented visual stimulus as "seen" if a response was received within said preliminary response time window, and otherwise as "not seen", and
   after the presentation of visual stimuli has been terminated:
   determining at least one final subject-adapted response time window based on recorded times of reception of previously received responses,
   finally classifying at least one of the preliminarily classified visual stimuli by applying said at least one final subject-adapted response time window modified by a factor, the value of which depends on said at least one of the preliminarily classified visual stimuli, said at least one of the preliminarily classified visual stimuli being finally classified as "seen" if the associated response was received within the modified final subject-adapted response time window and otherwise as "not seen".

13. A method according to claim 12, wherein the step of determining at least one final subject-adapted response time window and modifying it by a factor further comprises the steps
   dividing said previously received responses into groups, and for each group:
   assuming that the recorded times of reception are distributed according to a distribution of non-negative random variables,
   computing the mean value and the standard deviation of same distribution of non-negative random variables as well as the mean value of the strengths of the visual stimuli,
   interpolating said mean values of said distribution and of the strengths, respectively, for determining an individual mean value of said distribution for each visual stimulus within each of said groups and an individual mean value of the strengths for each visual stimulus within each of said groups, respectively,
   computing said modified final subject-adapted response time window for each visual stimulus within each of said groups based on the corresponding individual mean value of the recorded response times and the strength for said each visual stimulus, and on the standard deviation of the group to which said each visual stimulus belongs.

14. A method according to claim 13, further comprising the steps of:
   comparing the length of each said modified final subject-adapted response time window with the time period between the stimulus to which it pertains and the following stimulus,
   counting the number of said modified final subject-adapted response time windows having a length exceeding said time period between the stimulus to which it pertains and the following stimulus by more than a predetermined amount, and
   indicating a warning when said number is greater than a predetermined number.

15. A method according to claim 12, further comprising the steps of:
   determining at least one preliminary subject-adapted response time window based on recorded times of reception of previously received responses,
   applying said at lease one preliminary subject-adapted response time window for preliminarily classifying at least one visual stimulus presented subsequent to said determining of at least one preliminary subject-adapted response time window.

16. A method according to claim 12, wherein the frequency of false positive responses is determined from the number of responses received outside the modified final subject-adapted response time windows and the total time of testing minus the total time of the modified final subject-adapted response time windows.

17. A method of testing a subject's perception of successively presented visual stimuli, comprising the steps of:
   determining a preliminary response time window,
   presenting at least one visual stimulus to the subject, and for said at least one visual stimulus:
   waiting for a response during at most a predetermined time period,
   recording the time of reception of any response received from the subject within said predetermined time period,
   classifying a visual stimulus as "seen" if a response is received within said preliminary response time window and otherwise as "not seen",
   determining a subject-adapted response time window based on recorded times of reception of previously received responses,
   using said subject-adapted response time window for classifying at least one visual stimulus presented subsequent to said determining of said subject-adapted response time window,
   determining the frequency of false positive responses on the basis of the number of responses received outside the preliminary response time window and the subject-adapted response time window.

18. An apparatus for testing a subject's response to visual stimuli, comprising:
   means for successively presenting a plurality of visual stimuli to the subject;
   means for detecting whether the subject responds to each stimulus and, for each stimulus to which a response is detected, recording the time of the subject's response;
   means for determining a subject-adapted response time window based upon recorded times; and
   means for classifying the presented stimuli as "seen" or "not seen" in dependence upon whether a response to the stimulus was detected within the subject adapted response time window following the presentation of the stimulus.

19. An apparatus for testing a subject's perception of successively presented visual stimuli, comprising:
memory means for storing the responses from the subject to the stimuli; and a control unit which comprises:
means for determining a preliminary response time window,
means for presenting at least one visual stimulus to the subject, and for said at least one visual stimulus:
waiting for a response during at most a predetermined time period,
recording the time of reception of any response received from the subject within said predetermined time period,
preliminarily classifying said at least one visual stimulus as "seen" if a response is received within said preliminary response time window and otherwise as "not seen",
means for determining a subject-adapted response time window based on recorded times of reception of previously received responses,
means for classifying anew said at least one preliminarily classified visual stimulus by applying the subject-adapted response time window, said at least one preliminarily classified visual stimulus being classified as "seen" if the associated response was received within said subject-adapted response time window, and otherwise as "not seen".

20. An apparatus according to claim 19, further comprising means for modifying the response time windows by a factor, the value of which depends on the strength of said each presented visual stimulus.

21. An apparatus for testing a subject's perception of successively presented visual stimuli, each stimulus having a selected strength comprising:
means for determining a preliminary response time window,
means for presenting a plurality of visual stimuli to the subject, and for a presented visual stimulus:
modifying the preliminary response time window by a factor, the value of which depends on the strength of said presented visual stimulus,
waiting for a response during at most a predetermined time period,
recording the time of reception of any response received from the subject within said predetermined time period,
preliminary classifying said presented visual stimulus as "seen" if a response was received within said preliminary response time window, and otherwise as "not seen", and
means for determining at least one final subject-adapted response time window based on recorded times of reception of previously received responses,
means for finally classifying at least one of the preliminarily classified visual stimuli by applying said at least one final subject-adapted response time window modified by a factor, the value of which depends on the strength of said at least one of the preliminarily classified visual stimuli, said at least one of the preliminarily classified visual stimuli being finally classified as "seen" if the associated response was received within the modified final subject-adapted response time window axed otherwise as "not seen".

22. An apparatus for testing a subject's perception of successively presented visual stimuli comprising:
means for determining a preliminary response time window,
means for presenting at least one visual stimulus to the subject, and for said at least one visual stimulus:
waiting for a response during at most a predetermined time period,
recording the time of reception of any response received from the subject within said predetermined time period,
classifying a visual stimulus as "seen" if a response is received within said preliminary response time window and otherwise as "not seen",
means for determining a subject-adapted response time window based on recorded times of reception of previously received responses,
means for using said subject-adapted response time window for classifying at least one visual stimulus presented subsequent to said determining of said subject-adapted response time window,
means for determining the frequency of false positive responses on the basis of the number of responses received outside the preliminary response time window and the subject-adapted response time window.

* * * * *